United States Patent [19]

Wellenstam

[11] Patent Number: 4,528,982
[45] Date of Patent: Jul. 16, 1985

[54] HEAD ASSEMBLY FOR A VEIN STRIPPER

[75] Inventor: Kjell I. Wellenstam, Gothenburg, Sweden

[73] Assignee: Astra Meditec Aktiebolag, Molndal, Sweden

[21] Appl. No.: 556,585

[22] Filed: Nov. 30, 1983

[30] Foreign Application Priority Data

Jan. 7, 1983 [SE] Sweden .............................. 8300071

[51] Int. Cl.³ .......................................... A61B 17/00
[52] U.S. Cl. ............................................. 128/303 R
[58] Field of Search .................... 128/303 R, 304, 305

[56] References Cited

U.S. PATENT DOCUMENTS

| D. 237,116 | 10/1975 | Ekbladh | D83/12 R |
|---|---|---|---|
| 2,756,752 | 7/1956 | Scherlis | 128/303 |
| 2,779,334 | 1/1957 | Sandborn | 128/303 |
| 2,788,787 | 4/1957 | Trace | 128/303 |
| 2,863,458 | 12/1958 | Modny et al. | 128/303 |
| 2,868,206 | 1/1959 | Stoesser | 128/303 |
| 3,185,155 | 5/1965 | Slaten et al. | 128/303 |
| 3,508,553 | 4/1970 | Kanbar et al. | 128/303 |
| 3,659,606 | 5/1972 | Reimels | 128/303 R |
| 3,741,214 | 6/1973 | Tillander | 128/303 R |
| 3,764,427 | 10/1973 | Reimels | 156/73 |
| 3,788,325 | 1/1974 | Jacobsen | 128/303 R |

FOREIGN PATENT DOCUMENTS 1371176 10/1974 United Kingdom .

OTHER PUBLICATIONS

*Aloe Medical Instruments*, Catalog No. 220, 1966, p. 45, B1721, B1719, and B1718 vein strippers.

Primary Examiner—W. J. Shine
Attorney, Agent, or Firm—Brumbaugh, Graves, Donohue & Raymond

[57] ABSTRACT

A head assembly for a vein stripping instrument is described comprising a head lockable over an enlarged portion of a vein stripper cable by means of a snap mechanism and a cap.

4 Claims, 17 Drawing Figures

HEAD ASSEMBLY FOR A VEIN STRIPPER

TECHNICAL FIELD

The present invention is related to a head assembly for a vein stripping instrument. Vein strippers or vein extractors are used in surgery for extracting veins, primarily veins in the extremities affected by varices or phlebectasies.

PRIOR ART

British Pat. No. 1 290 282 describes a varices bougie provided with a head or body at one end and having the opposite end shaped as a helix.

A vein stripper having a head releasably attached, in which head the cable or wire may be entered through a longitudinal slot, is described in British Pat. No. 1 371 176. U.S. Pat. No. 3,764,427 describes a vein stripper wherein a conical head can be releasably mounted on an enlarged end portion of a cable. A vein stripper with a releasable head is advantageous in providing for introduction of the stripper cable into the vein in one direction, assembling a head at the front end of said cable and extracting the vein and stripper in the direction opposite to the direction of introduction. Such previously known vein strippers, however, have the drawback that the head cannot be securely attached to the cable and may thus be released by accident, e.g. when the surgeon relaxes the instrument during the extraction operation or when pushing the stripper backwards.

DISCLOSURE OF INVENTION

The object of the present invention is to provide for a vein stripper having a head attachable at one or both ends of a stripper cable and being releasable therefrom, such head being safely fixed when attached to the cable. Further objects are to provide for a vein stripper in which the head can be easily and quickly attached to the end of the stripper and wherein the end of the cable at which the head is to be attached is smooth and can be designed in such manner that the introduction thereof through the veins is facilitated.

DETAILED DISCLOSURE OF THE INVENTION

The objects of the present invention are successfully fulfilled by providing a head assembly for a vein stripping instrument comprising a head having a longitudinal slot extending into a central bore, wherein a cable of a vein stripper can be received, said bore having an enlarged portion opening at a distal end of the head, said head having one or more hook means projecting from the distal end thereof and being lockable over an edge of a cap member, said cap member and head forming a head assembly lockable at an enlarged end portion of the vein stripper cable.

In the head assembly the cap member is preferably of cylindrical shape and has a lateral opening for each hook means of the head. Preferably the hook means of the head are lockable over an inner edge of the cap member by snapping out in a radial direction. In a preferred embodiment of the invention the hook means projecting from the distal end of the head consist of two hooks placed opposite to each other.

The invention is further described with reference to the enclosed drawings wherein

Figure 1:
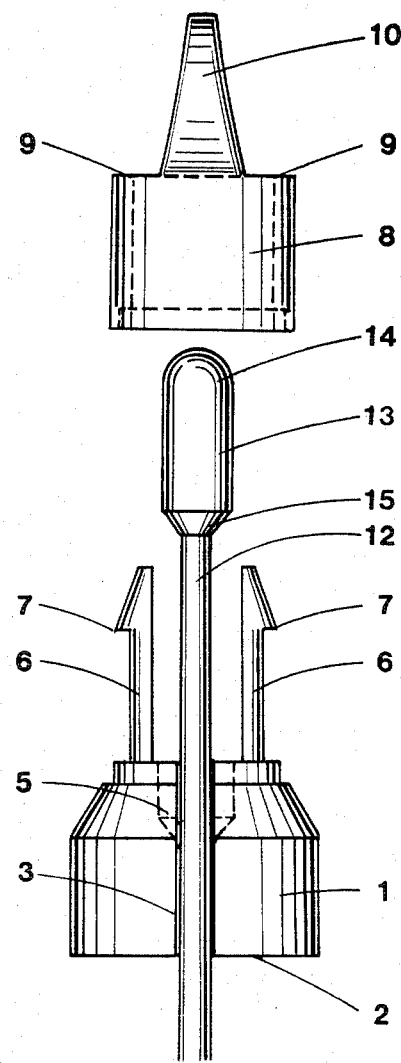
FIG. 1 is an exploded view of a head assembly for a vein stripping instrument according to the invention, and an end portion of a vein stripper cable.

In the drawings a head of a vein stripper is denoted 1. Said head has a proximal end surface 2 which will engage the vein to be extracted. A longitudinal slot 3 extends into a central bore 4 having an enlarged distal portion 5. From the distal end of the head two integrally formed hook members 6 project having lateral edges 7. A cap 8 has the shape of an open cylinder having edges 9 and a bridging tapered end portion 10.

A vein stripper cable 12 has a cylindrical enlarged end portion 13 with a rounded distal end 14 and a conical proximal segment 15. The cable 12 is introduced through the slot 3 into the central bore 4 of the head and the enlarged end portion 13 is pulled into the enlarged distal portion 5 of the bore. The cap 8 is pressed over the hooks 6, which are of sufficient flexibility to yield inwards and snap back to a position where the edges 7 are in locking relationship with the edges 9 of the cap, thus forming a head assembly firmly locked over the end portion 13 of the cable.

Figure 2A:
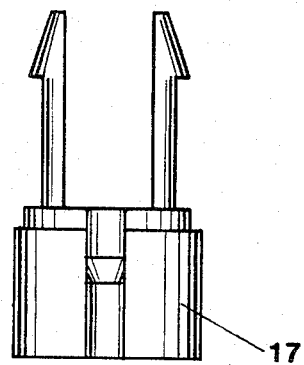
FIGS. 2a and 2b show heads of different size that can be substituted for the corresponding part in the article of FIG. 1.
Figure 2B:
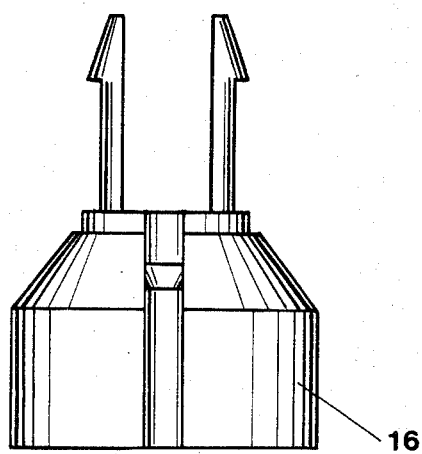
Figure 3:
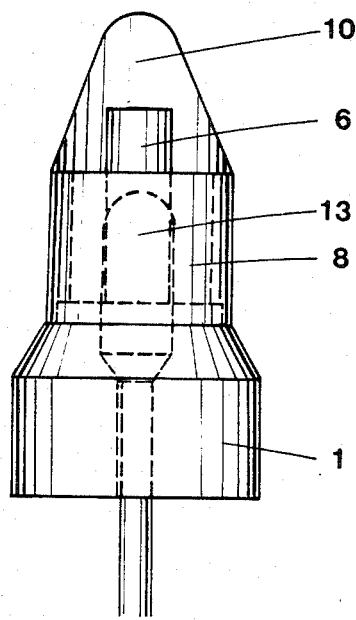
FIG. 3 is a side view taken at 90° angle to the view of FIG. 1, showing the assembly fixed at the end of a vein stripper cable.
Figure 4:
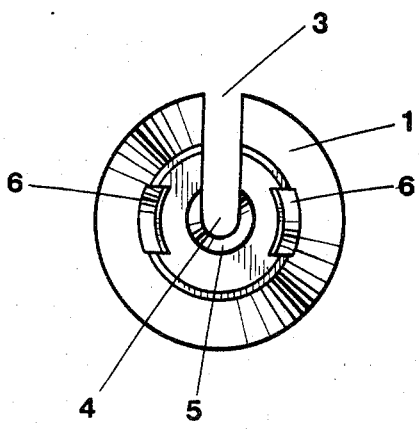
FIG. 4 is a view of a head of an assembly shown in FIG. 1, taken from the distal end thereof.
Figure 5:
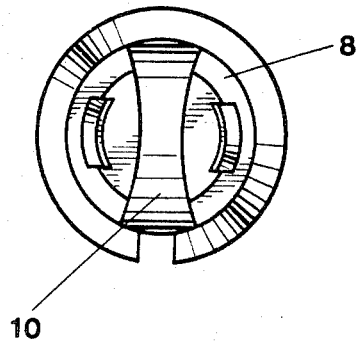
FIG. 5 is an end view of the assembly shown in FIG. 3.

As shown in FIG. 2, the head 1 can be substituted with a head of larger diameter 16 or a head of smaller diameter 17 if required. The same cap 8 may be used.

Figure 6:
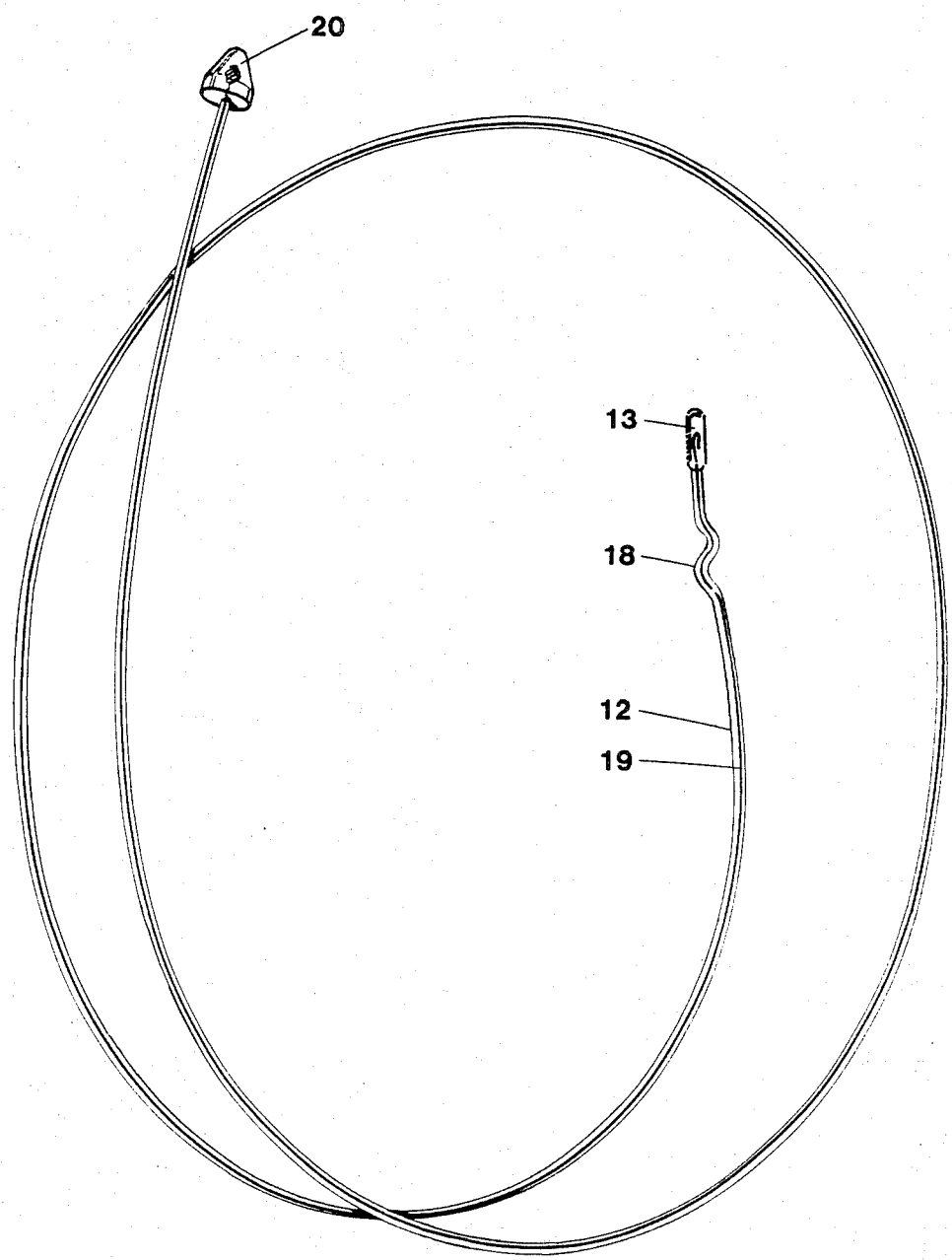
FIG. 6 shows a vein stripper cable for use with a head assembly according to the invention.

The vein stripper cable shown in FIG. 6 has a helical portion 18 spaced from the enlarged end portion 13 by a short straight segment. The cable is made up of a tube of plastic material and reinforced with a steel wire 19. At the end opposite to portion 13 the cable is provided with a conventional vein stripper head 20, thus enabling vein extraction in the direction of introduction in cases when the surgeon finds such manner of extraction preferable. In the alternative, said opposite end may have another enlarged end portion 13 or the end may be shaped for attachment to a handle.

The head assembly may be prepared of a plastic material such as acetal polymer or polyamide by injection moulding.

The dimensions of the enlarged end portion 13 of the cable and the corresponding cavity in the head 1 are preferably chosen thus that the head wil be firmly held after pressing the end portion into the cap 8.

I claim:

1. A head assembly for a vein stripping instrument comprising a head having a longitudinal slot extending into a central bore wherein a cable of a vein stripper can be received, said bore having an enlarged portion opening at a distal end of the head, said head having one or more hook means projecting from the distal end thereof and being lockable over an edge of a cap member, said cap member and head forming a head assembly lockable at an enlarged end portion of the vein stripper cable.

2. A head assembly according to claim 1 wherein the cap member is of cylindrical shape and has a lateral opening for each hook means of the head.

3. A head assembly according to claim 1 or 2, wherein the hook means of the head are lockable over an inner edge of the cap member by snapping out in a radial direction.

4. A head assembly according to claim 1 or 2 wherein the hook means projecting from the distal end of the head consist of two hooks.

* * * * *